United States Patent
Kobayashi

(10) Patent No.: US 10,202,333 B2
(45) Date of Patent: Feb. 12, 2019

(54) AQUEOUS SOLUTION CONTAINING BIS(N EPSILON LAUROYLLYSINE)DICARBOXYLIC ACID DIAMIDE AND/OR SALT THEREOF, AND METHOD FOR PRODUCING SAME

(71) Applicant: AJINOMOTO CO., INC., Tokyo (JP)

(72) Inventor: Shun Kobayashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 108 days.

(21) Appl. No.: 15/481,022

(22) Filed: Apr. 6, 2017

(65) Prior Publication Data

US 2017/0260127 A1 Sep. 14, 2017

Related U.S. Application Data

(63) Continuation of application No. PCT/JP2015/078288, filed on Oct. 6, 2015.

(30) Foreign Application Priority Data

Oct. 7, 2014 (JP) ................................ 2014-206548

(51) Int. Cl.
*C07C 231/02* (2006.01)
*C07C 231/22* (2006.01)
*C07C 233/47* (2006.01)
*A61K 8/44* (2006.01)
*A61Q 19/00* (2006.01)

(52) U.S. Cl.
CPC ............ *C07C 231/02* (2013.01); *A61K 8/442* (2013.01); *A61Q 19/00* (2013.01); *C07C 231/22* (2013.01); *C07C 233/47* (2013.01)

(58) Field of Classification Search
USPC ........................................................ 424/400
See application file for complete search history.

(56) References Cited

U.S. PATENT DOCUMENTS

| 2004/0248812 A1 | 12/2004 | Hanabusa et al. |
| 2014/0350128 A1 | 11/2014 | Hanabusa et al. |
| 2017/0281495 A1 | 10/2017 | Haraya et al. |

FOREIGN PATENT DOCUMENTS

| CN | 1541998 A | 11/2004 |
| EP | 1 473 027 A1 | 11/2004 |
| EP | 3 238 700 A1 | 11/2017 |
| JP | 2004-323505 A | 11/2004 |
| WO | WO 2013/118896 A1 | 8/2013 |

OTHER PUBLICATIONS

International Preliminary Report on Patentability and Written Opinion dated Apr. 11, 2017 in PCT/JP2015/078288 (With English translation).
Masahiro Suzuki, et al. "Novel Dumbbell-form low-molecular-weight gelators based on L-lysine: their hydrogelation and organogelation properties" New J. Chem, vol. 29, No. 11, 2005, pp. 1439-1444.
Liang Ya-Qin, et al. "Surface Activity Properties of Chiral L-Lysine Based Gemini Surfactants" Chemical Journal of Chinese Universities, vol. 34, No. 12, 2013, pp. 2783 to 2790 (with English Abstract).
Yaqin Liang, et al. "Surface Adsorption and Aggregation Properties of Novel L-Lysine- Based Gemini Surfactants" Journal of Surfactants and Detergents, vol. 17, No. 4, 2013, pp. 693 to 701.
Combined Chinese Office Action and Search Report dated Jul. 30, 2018 in Chinese Patent Application No. 201550054750.X (with English translation of Category of Cited Documents), citing document AO therein, 8 pages.
Extended European Search Report dated Apr. 20, 2018 in Patent Application No. 15848403.0.

*Primary Examiner* — Nannette Holloman
(74) *Attorney, Agent, or Firm* — Oblon, McClelland, Maier & Neustadt, L.L.P.

(57) ABSTRACT

The present invention provides a method of producing an aqueous solution containing bis($N^\varepsilon$-lauroyl lysine)dicarboxylic acid diamide and/or a salt thereof, and having a pH of 9-11, which includes a first step of reacting $N^\varepsilon$-lauroyl lysine and/or a salt thereof with dicarboxylic acid dichloride in a water solvent having a pH of 12-14 to form bis($N^\varepsilon$-lauroyl lysine)dicarboxylic acid diamide and/or a salt thereof, a second step of adjusting the aqueous solution obtained in the first step to pH 7.5-8.5, a third step of adding $N^\varepsilon$-lauroyl lysine to the aqueous solution obtained in the second step and filtering the mixture, and a fourth step of adjusting the aqueous solution obtained in the third step to pH 9-11.

17 Claims, No Drawings

AQUEOUS SOLUTION CONTAINING BIS(N EPSILON LAUROYLLYSINE)DICARBOXYLIC ACID DIAMIDE AND/OR SALT THEREOF, AND METHOD FOR PRODUCING SAME

CROSS REFERENCES TO RELATED APPLICATIONS

This application is a continuation of International Patent Application No. PCT/JP2015/078288, filed on Oct. 6, 2015, and claims priority to Japanese Patent Application No. 2014-206548, filed on Oct. 7, 2014, both of which are incorporated herein by reference in their entireties.

BACKGROUND OF THE INVENTION

Field of the Invention

The present invention relates to an aqueous solution containing bis($N^\varepsilon$-lauroyl lysine)dicarboxylic acid diamide and/or a salt thereof, and a production method thereof.

Discussion of the Background

It has been reported that bis($N^\varepsilon$-lauroyl lysine)dicarboxylic acid diamide and a salt thereof are useful as gelling agents for water and organic solvents (non-patent document 1). In non-patent document 1, $N^\varepsilon$-lauroyl-L-lysine and dicarboxylic acid dichloride are reacted in a mixed solvent of water and diethyl ether, the reaction solution is acidified with hydrochloric acid, and the resultant product is precipitated and filtrated, whereby bis($N^\varepsilon$-lauroyl lysine)dicarboxylic acid diamide is produced. Furthermore, a salt thereof is produced by adding a base (non-patent document 1, page 1440, Scheme 1 and page 1442, General procedure).

DOCUMENT LIST

Non-Patent Document non-patent document 1: New J. Chem., 2005, 29, 1439-1444

SUMMARY OF THE INVENTION

Problems to be Solved by the Invention

Use of bis($N^\varepsilon$-lauroyl lysine)dicarboxylic acid diamide and/or a salt thereof as a material for cosmetics, particularly skin lotion and the like, has been considered. For the production of skin lotion and the like, it is preferable to react $N^\varepsilon$-lauroyl-L-lysine and dicarboxylic acid dichloride in a water solvent rather than a mixed solvent of water and an organic solvent such as the one described in non-patent document 1, to directly produce an aqueous solution containing bis($N^\varepsilon$-lauroyl lysine)dicarboxylic acid diamide and/or a salt thereof, and directly use the obtained aqueous solution as a material. To use the produced above-mentioned aqueous solution as it is as a material, it is necessary to prevent easy occurrence of precipitation.

The present invention has been made taking note of the above-mentioned situation, and an object thereof is to provide an aqueous solution containing bis($N^\varepsilon$-lauroyl lysine)dicarboxylic acid diamide and/or a salt thereof, which does not show precipitation with ease, and a production method thereof.

Means of Solving the Problems

The present inventor has conducted intensive studies in an attempt to achieve the above-mentioned object and found that the precipitate of an aqueous solution containing bis($N^\varepsilon$-lauroyl lysine)dicarboxylic acid diamide and/or a salt thereof is $N^\varepsilon$-lauroyl lysine and/or a salt thereof, and the generation of the precipitate can be suppressed by reducing the residue of the compound. In addition, according to the following production method of the aqueous solution containing bis($N^\varepsilon$-lauroyl lysine)dicarboxylic acid diamide and/or a salt thereof, which is based on the finding, the generation of precipitation in the obtained aqueous solution can be suppressed by reducing the residue of $N^\varepsilon$-lauroyl lysine and/or a salt thereof. The present invention based on such finding is as described below.

[1] A method of producing an aqueous solution comprising bis($N^\varepsilon$-lauroyl lysine)dicarboxylic acid diamide and/or a salt thereof, and having a pH of 9-11, which comprises
  a first step of reacting $N^\varepsilon$-lauroyl lysine and/or a salt thereof with dicarboxylic acid dichloride in a water solvent having a pH of 12-14 to form bis($N^\varepsilon$-lauroyl lysine)dicarboxylic acid diamide and/or a salt thereof,
  a second step of adjusting the aqueous solution obtained in the first step to pH 7.5-8.5,
  a third step of adding $N^\varepsilon$-lauroyl lysine to the aqueous solution obtained in the second step and filtering the mixture, and
  a fourth step of adjusting the aqueous solution obtained in the third step to pH 9-11.

[2] The production method of the aforementioned [1], wherein the pH of the water solvent containing the reaction product in the first step is 12.5-14.

[3] The production method of the aforementioned [1], wherein the pH of the water solvent containing the reaction product in the first step is 13-14.

[4] The production method of any one of the aforementioned [1]-[3], wherein the water solvent is substantially free of a hydrophilic organic solvent.

[5] The production method of any one of the aforementioned [1]-[3], wherein the water solvent has a hydrophilic organic solvent content of not more than 5 wt %, or is free of a hydrophilic organic solvent.

[6] The production method of any one of the aforementioned [1]-[3], wherein the water solvent has a hydrophilic organic solvent content of not more than 4 wt %, or is free of a hydrophilic organic solvent.

[7] The production method of any one of the aforementioned [1]-[3], wherein the water solvent has a hydrophilic organic solvent content of not more than 3 wt %, or is free of a hydrophilic organic solvent.

[8] The production method of any one of the aforementioned [1]-[3], wherein the water solvent has a hydrophilic organic solvent content of not more than 2 wt %, or is free of a hydrophilic organic solvent.

[9] The production method of any one of the aforementioned [1]-[8], wherein the $N^\varepsilon$-lauroyl lysine and/or a salt thereof are/is an alkali metal salt(s) of $N^\varepsilon$-lauroyl lysine.

[10] The production method of any one of the aforementioned [1]-[8], wherein the $N^\varepsilon$-lauroyl lysine and/or a salt thereof are/is a sodium salt(s) of $N^\varepsilon$-lauroyl lysine.

[11] The production method of any one of the aforementioned [1]-[10], wherein the dicarboxylic acid dichloride is at least one selected from the group consisting of suberic acid dichloride, azelaic acid dichloride and sebacic acid dichloride.

[12] The production method of any one of the aforementioned [1]-[10], wherein the dicarboxylic acid dichloride is suberic acid dichloride, azelaic acid dichloride, or sebacic acid dichloride.

[13] The production method of any one of the aforementioned [1]-[10], wherein the dicarboxylic acid dichloride is sebacic acid dichloride.
[14] The production method of any one of the aforementioned [1]-[13], wherein the bis($N^\varepsilon$-lauroyl lysine)dicarboxylic acid diamide is bis($N^\varepsilon$-lauroyl lysine)suberic acid diamide, bis($N^\varepsilon$-lauroyl lysine)azelaic acid diamide, or bis($N^\varepsilon$-lauroyl lysine)sebacic acid diamide.
[15] The production method of any one of the aforementioned [1]-[13], wherein the bis($N^\varepsilon$-lauroyl lysine)dicarboxylic acid diamide is bis($N^\varepsilon$-lauroyl lysine)sebacic acid diamide.
[16] The production method of any one of the aforementioned [1]-[15], wherein the salt of the bis($N^\varepsilon$-lauroyl lysine) dicarboxylic acid diamide is an alkali metal salt.
[17] The production method of any one of the aforementioned [1]-[15], wherein the salt of the bis($N^\varepsilon$-lauroyl lysine) dicarboxylic acid diamide is a sodium salt.
[18] The production method of any one of the aforementioned [1]-[13], wherein the bis($N^\varepsilon$-lauroyl lysine)dicarboxylic acid diamide and/or a salt thereof are/is a sodium salt(s) of bis($N^\varepsilon$-lauroyl lysine)suberic acid diamide, a sodium salt(s) of bis($N^\varepsilon$-lauroyl lysine)azelaic acid diamide, or a sodium salt(s) of bis($N^\varepsilon$-lauroyl lysine)sebacic acid diamide.
[19] The production method of any one of the aforementioned [1]-[13], wherein the bis($N^\varepsilon$-lauroyl lysine)dicarboxylic acid diamide and/or a salt thereof are/is a bis($N^\varepsilon$-lauroyl lysine)suberic acid diamide disodium salt(s), a bis($N^\varepsilon$-lauroyl lysine)azelaic acid diamide disodium salt(s), or a bis ($N^\varepsilon$-lauroyl lysine)sebacic acid diamide disodium salt(s).
[20] The production method of any one of the aforementioned [1]-[13], wherein the bis($N^\varepsilon$-lauroyl lysine)dicarboxylic acid diamide and/or a salt thereof are/is a bis($N^\varepsilon$-lauroyl lysine)sebacic acid diamide disodium salt(s).
[21] The production method of any one of the aforementioned [1]-[20], wherein the pH of the aqueous solution obtained in the first step is adjusted to 7.6-8.3 in the second step.
[22] The production method of any one of the aforementioned [1]-[20], wherein the pH of the aqueous solution obtained in the first step is adjusted to 7.7-8.0.
[23] The production method of any one of the aforementioned [1]-[22], wherein the amount of the $N^\varepsilon$-lauroyl lysine added in the third step is 0.02-0.04 mol per 1 mol of the $N^\varepsilon$-lauroyl lysine and/or a salt thereof used in the first step (1 mol of the total of both when they are used).
[24] The production method of any one of the aforementioned [1]-[22], wherein the amount of the $N^\varepsilon$-lauroyl lysine added in the third step is 0.025-0.03 mol per 1 mol of the $N^\varepsilon$-lauroyl lysine and/or a salt thereof used in the first step (1 mol of the total of both when they are used).
[25] The production method of any one of the aforementioned [1]-[24], wherein the pH of the aqueous solution obtained in the third step is adjusted to 9.5-10.5 in the fourth step.
[26] The production method of any one of the aforementioned [1]-[24], wherein the pH of the aqueous solution obtained in the third step is adjusted to 9.8-10.2 in the fourth step.
[27] The production method of any one of the aforementioned [1]-[26], wherein the aqueous solution obtained in the fourth step has a content of the $N^\varepsilon$-lauroyl lysine and/or a salt thereof of not more than 0.016 wt %, and a content of the bis($N^\varepsilon$-lauroyl lysine)dicarboxylic acid diamide and/or a salt thereof of 5-20 wt %.

[28] The production method of the aforementioned [27], wherein the content of the $N^\varepsilon$-lauroyl lysine and/or a salt thereof in the aqueous solution obtained in the fourth step is not more than 0.013 wt %.
[29] The production method of the aforementioned [27], wherein the content of the $N^\varepsilon$-lauroyl lysine and/or a salt thereof in the aqueous solution obtained in the fourth step is not more than 0.01 wt %.
[30] The production method of the aforementioned [27], wherein the content of the bis($N^C$-lauroyl lysine)dicarboxylic acid diamide and/or a salt thereof in the aqueous solution obtained in the fourth step is 7-15 wt %.
[31] The production method of the aforementioned [27], wherein the content of the bis($N^\varepsilon$-lauroyl lysine)dicarboxylic acid diamide and/or a salt thereof in the aqueous solution obtained in the fourth step is 8-12 wt %.
[32] An aqueous solution comprising 5-20 wt % of bis($N^\varepsilon$-lauroyl lysine)dicarboxylic acid diamide and/or a salt thereof and having a pH of 9-11, which has a content of $N^\varepsilon$-lauroyl lysine and/or a salt thereof of not more than 0.016 wt %.
[33] The aqueous solution of the aforementioned [32], wherein the content of the bis($N^\varepsilon$-lauroyl lysine)dicarboxylic acid diamide and/or a salt thereof is 7-15 wt %.
[34] The aqueous solution of the aforementioned [32], wherein the content of the bis($N^\varepsilon$-lauroyl lysine)dicarboxylic acid diamide and/or a salt thereof is 8-12 wt %.
[35] The aqueous solution of any one of the aforementioned [32]-[34], wherein the pH is 9.5-10.5.
[36] The aqueous solution of any one of the aforementioned [32]-[34], wherein the pH is 9.8-10.2.
[37] The aqueous solution of any one of the aforementioned [32]-[36], wherein the content of the $N^\varepsilon$-lauroyl lysine and/or a salt thereof is not more than 0.013 wt %.
[38] The aqueous solution of any one of the aforementioned [32]-[36], wherein the content of the $N^\varepsilon$-lauroyl lysine and/or a salt thereof is not more than 0.01 wt %.
[39] The aqueous solution of any one of the aforementioned [32]-[38], wherein the bis($N^\varepsilon$-lauroyl lysine)dicarboxylic acid diamide is bis($N^\varepsilon$-lauroyl lysine)suberic acid diamide, bis($N^\varepsilon$-lauroyl lysine)azelaic acid diamide, or bis($N^\varepsilon$-lauroyl lysine)sebacic acid diamide.
[40] The aqueous solution of any one of the aforementioned [32]-[38], wherein the bis($N^\varepsilon$-lauroyl lysine)dicarboxylic acid diamide is bis($N^\varepsilon$-lauroyl lysine)sebacic acid diamide.
[41] The aqueous solution of any one of the aforementioned [32]-[40], wherein the salt of the bis($N^\varepsilon$-lauroyl lysine) dicarboxylic acid diamide is an alkali metal salt.
[42] The aqueous solution of any one of the aforementioned [32]-[40], wherein the salt of the bis($N^\varepsilon$-lauroyl lysine) dicarboxylic acid diamide is a sodium salt.
[43] The aqueous solution of any one of the aforementioned [32]-[38], wherein the bis($N^\varepsilon$-lauroyl lysine)dicarboxylic acid diamide and/or a salt thereof are/is a sodium salt(s) of bis($N^\varepsilon$-lauroyl lysine)suberic acid diamide, a sodium salt(s) of bis($N^\varepsilon$-lauroyl lysine)azelaic acid diamide, or a sodium salt(s) of bis($N^\varepsilon$-lauroyl lysine)sebacic acid diamide.
[44] The aqueous solution of any one of the aforementioned [32]-[38], wherein the bis($N^\varepsilon$-lauroyl lysine)dicarboxylic acid diamide and/or a salt thereof are/is a bis($N^\varepsilon$-lauroyl lysine)suberic acid diamide disodium salt(s), a bis($N^\varepsilon$-lauroyl lysine)azelaic acid diamide disodium salt(s), or a bis ($N^\varepsilon$-lauroyl lysine)sebacic acid diamide disodium salt(s).
[45] The aqueous solution of any one of the aforementioned [32]-[38], wherein the bis($N^\varepsilon$-lauroyl lysine)dicarboxylic acid diamide and/or a salt thereof are/is a bis($N^\varepsilon$-lauroyl lysine)sebacic acid diamide disodium salt(s).

[46] The aqueous solution of any one of the aforementioned [32]-[45], which has a content of ($N^\varepsilon$-lauroyl lysine)dicarboxylic acid monoamide and/or a salt thereof of not more than 1.0 wt %.
[47] The aqueous solution of any one of the aforementioned [32]-[45], which has a content of ($N^\varepsilon$-lauroyl lysine)dicarboxylic acid monoamide and/or a salt thereof of 0.1-1.0 wt %.
[48] The aqueous solution of any one of the aforementioned [32]-[45], wherein the content of the ($N^\varepsilon$-lauroyl lysine) dicarboxylic acid monoamide and/or a salt thereof is 0.2-0.6 wt %.
[49] The aqueous solution of any one of the aforementioned [46]-[48], wherein the ($N^\varepsilon$-lauroyl lysine)dicarboxylic acid monoamide is ($N^\varepsilon$-lauroyl lysine)suberic acid monoamide, ($N^\varepsilon$-lauroyl lysine)azelaic acid monoamide, or ($N^\varepsilon$-lauroyl lysine)sebacic acid monoamide.
[50] The aqueous solution of any one of the aforementioned [46]-[48], wherein the ($N^\varepsilon$-lauroyl lysine)dicarboxylic acid monoamide is ($N^\varepsilon$-lauroyl lysine)sebacic acid monoamide.
[51] The aqueous solution of any one of the aforementioned [46]-[50], wherein the salt of the ($N^\varepsilon$-lauroyl lysine)dicarboxylic acid monoamide is an alkali metal salt.
[52] The aqueous solution of any one of the aforementioned [46]-[50], wherein the salt of the ($N^\varepsilon$-lauroyl lysine)dicarboxylic acid monoamide is a sodium salt.
[53] The aqueous solution of any one of the aforementioned [46]-[48], wherein the ($N^\varepsilon$-lauroyl lysine)dicarboxylic acid monoamide and/or a salt thereof are/is a sodium salt(s) of ($N^\varepsilon$-lauroyl lysine)suberic acid monoamide, a sodium salt(s) of ($N^\varepsilon$-lauroyl lysine)azelaic acid monoamide, or a sodium salt(s) of ($N^\varepsilon$-lauroyl lysine)sebacic acid monoamide.
[54] The aqueous solution of any one of the aforementioned [46]-[48], wherein the ($N^\varepsilon$-lauroyl lysine)dicarboxylic acid monoamide and/or a salt thereof are/is a ($N^\varepsilon$-lauroyl lysine) suberic acid monoamide disodium salt(s), a ($N^\varepsilon$-lauroyl lysine)azelaic acid monoamide disodium salt(s), or a ($N^\varepsilon$-lauroyl lysine)sebacic acid monoamide disodium salt(s).
[55] The aqueous solution of any one of the aforementioned [46]-[48], wherein the ($N^\varepsilon$-lauroyl lysine)dicarboxylic acid monoamide and/or a salt thereof are/is a ($N^\varepsilon$-lauroyl lysine) sebacic acid monoamide disodium salt(s).
[56] The aqueous solution of any one of the aforementioned [32]-[55], which has a content of dicarboxylic acid and/or a salt thereof of not more than 0.5 wt %.
[57] The aqueous solution of any one of the aforementioned [32]-[55], which has a content of dicarboxylic acid and/or a salt thereof of 0.01-0.5 wt %.
[58] The aqueous solution of any one of the aforementioned [32]-[55], which has a content of dicarboxylic acid and/or a salt thereof of 0.1-0.4 wt %.
[59] The aqueous solution of any one of the aforementioned [56]-[58], wherein the dicarboxylic acid is at least one selected from the group consisting of suberic acid, azelaic acid and sebacic acid.
[60] The aqueous solution of any one of the aforementioned [56]-[58], wherein the dicarboxylic acid is suberic acid, azelaic acid, or sebacic acid.
[61] The aqueous solution of any one of the aforementioned [56]-[58], wherein the dicarboxylic acid is sebacic acid.
[62] The aqueous solution of any one of the aforementioned [56]-[61], wherein the salt of the dicarboxylic acid is an alkali metal salt.
[63] The aqueous solution of any one of the aforementioned [56]-[61], wherein the salt of the dicarboxylic acid is a sodium salt.
[64] The aqueous solution of any one of the aforementioned [56]-[58], wherein the dicarboxylic acid and/or a salt thereof is a sodium salt of suberic acid, a sodium salt of azelaic acid, or a sodium salt of sebacic acid.
[65] The aqueous solution of any one of the aforementioned [56]-[58], wherein the dicarboxylic acid and/or a salt thereof is suberic acid disodium, azelaic acid disodium, or sebacic acid disodium.
[66] The aqueous solution of any one of the aforementioned [56]-[58], wherein the dicarboxylic acid and/or a salt thereof is sebacic acid disodium.
[67] The aqueous solution of any one of the aforementioned [32]-[66], which is put in a container.

Effect of the Invention

In the aqueous solution of the present invention containing bis($N^\varepsilon$-lauroyl lysine)dicarboxylic acid diamide and/or a salt thereof, since the content of the $N^\varepsilon$-lauroyl lysine and/or a salt thereof is reduced, the generation of precipitate is suppressed. According to the production method of the present invention, moreover, the aforementioned aqueous solution having a reduced content of $N^\varepsilon$-lauroyl lysine and/or a salt thereof is obtained.

DETAILED DESCRIPTION OF THE PREFERRED EMBODIMENTS

The production method of the present invention includes a first step of reacting $N^\varepsilon$-lauroyl lysine and/or a salt thereof with dicarboxylic acid dichloride in a water solvent having a pH of 12-14 to form bis($N^\varepsilon$-lauroyl lysine)dicarboxylic acid diamide and/or a salt thereof.

The pH of the water solvent containing the reaction product in the first step (i.e., reaction system) is 12-14, preferably 12.5-14, more preferably 13-14. While the base used to adjust the pH is not particularly limited, for example, sodium hydroxide, potassium hydroxide, calcium hydroxide, sodium carbonate, ammonia and the like can be mentioned. Only one kind of base may be used, or two or more kinds thereof may be used in combination. Of these, sodium hydroxide is preferable.

The water solvent used in the first step is preferably substantially free of a hydrophilic organic solvent (e.g., acetone, t-butanol, propylene glycol etc.). The water solvent being substantially free of a hydrophilic organic solvent means that the content of a hydrophilic organic solvent in the water solvent is not more than 5 wt %, or the water solvent does not contain a hydrophilic organic solvent. The content of a hydrophilic organic solvent in the water solvent is more preferably not more than 4 wt %, further preferably not more than 3 wt %, particularly preferably not more than 2 wt %. When a water solvent does not substantially contain a hydrophilic organic solvent, the obtained aqueous solution can be directly used as a material of skin lotion and the like.

In the first step, $N^\varepsilon$-lauroyl lysine may be used or a salt thereof may be used. $N^\varepsilon$-lauroyl lysine may be an L-form or D-form, preferably an L-form. Examples of the $N^\varepsilon$-lauroyl lysine salt include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt, and the like. $N^\varepsilon$-lauroyl lysine salt is preferably an alkali metal salt, more preferably a sodium salt.

Examples of the dicarboxylic acid dichloride to be used in the first step include oxalic acid dichloride, malonic acid dichloride, succinic acid dichloride, glutaric acid dichloride, adipic acid dichloride, pimelic acid dichloride, suberic acid dichloride, azelaic acid dichloride, sebacic acid dichloride, undecanedioic acid dichloride, dodecanedioic acid dichloride, phthalic acid dichloride, isophthalic acid dichloride, terephthalic acid dichloride and the like. One kind of these may be used, or two or more kinds thereof may be used in combination. Of these, suberic acid dichloride, azelaic acid dichloride, and sebacic acid dichloride are preferable, and sebacic acid dichloride is more preferable. The amount of dicarboxylic acid dichloride to be used is generally 0.4-0.6 mol per 1 mol of $N^\varepsilon$-lauroyl lysine and/or a salt thereof used in the first step (1 mol of the total of both when they are used). In the first step, it is preferable to add dicarboxylic acid dichloride dropwise while stirring the water solvent containing $N^\varepsilon$-lauroyl lysine and/or a salt thereof and a base.

The reaction time of the first step is preferably 15-90 min, more preferably 30-60 min, and the reaction temperature thereof is preferably 10-35° C., more preferably 15-30° C.

The bis($N^\varepsilon$-lauroyl lysine)dicarboxylic acid diamide formed in the first step (hereinafter sometimes to be abbreviated as "diamide") means a condensate formed by the reaction of 2 molecules of $N^\varepsilon$-lauroyl lysine with 1 molecule of dicarboxylic acid dichloride at the α position —$NH_2$ thereof, and the chemical structure thereof is represented by the following formula (1):

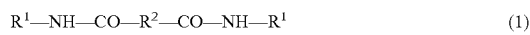

$$R^1—NH—CO—R^2—CO—NH—R^1 \qquad (1)$$

wherein $R^1$ is a monovalent organic group derived from $N^\varepsilon$-lauroyl lysine, and $R^2$ is a divalent organic group derived from dicarboxylic acid dichloride.

Examples of the diamide include bis($N^\varepsilon$-lauroyl lysine) oxalic acid diamide, bis($N^\varepsilon$-lauroyl lysine)malonic acid diamide, bis($N^\varepsilon$-lauroyl lysine)succinic acid diamide, bis ($N^\varepsilon$-lauroyl lysine)glutaric acid diamide, bis($N^\varepsilon$-lauroyl lysine)adipic acid diamide, bis($N^\varepsilon$-lauroyl lysine)pimelic acid diamide, bis($N^\varepsilon$-lauroyl lysine)suberic acid diamide, bis($N^E$-lauroyl lysine)azelaic acid diamide, bis($N^\varepsilon$-lauroyl lysine)sebacic acid diamide, bis($N^\varepsilon$-lauroyl lysine)undecanedioic acid diamide, bis($N^\varepsilon$-lauroyl lysine)dodecanedioic acid diamide, bis($N^\varepsilon$-lauroyl lysine)phthalic acid diamide, bis($N^\varepsilon$-lauroyl lysine)isophthalic acid diamide, bis($N^\varepsilon$-lauroyl lysine)terephthalic acid diamide and the like. Of these, bis($N^\varepsilon$-lauroyl lysine)suberic acid diamide, bis($N^\varepsilon$-lauroyl lysine)azelaic acid diamide, and bis($N^\varepsilon$-lauroyl lysine)sebacic acid diamide are preferable, and bis($N^\varepsilon$-lauroyl lysine) sebacic acid diamide is more preferable.

Examples of the salt of the diamide formed in the first step include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt and the like. The cation contained in the salt of the diamide is derived from the base used for the $N^\varepsilon$-lauroyl lysine salt used in the first step and/or pH adjustment.

In the salt of diamide, two carboxy groups may be in the form of a salt (—COOM, M is a counter cation), or only one carboxy group may be in the form of a salt. The salt of the diamide is preferably alkali metal salt, more preferably sodium salt (monosodium salt and/or disodium salt), further preferably disodium salt, particularly preferably bis($N^\varepsilon$-lauroyl lysine)sebacic acid diamide disodium salt.

The production method of the present invention includes the second step of adjusting the pH of the aqueous solution obtained in the first step to 7.5-8.5. The pH is preferably 7.6-8.3, more preferably 7.7-8.0. The acid to be used for pH adjustment is not particularly limited, and inorganic acids such as hydrochloric acid, hydrobromic acid, sulfuric acid, phosphoric acid and the like; organic acids such as carboxylic acid (e.g., acetic acid, citric acid), sulfonic acid and the like; can be used. Only one kind of acid may be used, or two or more kinds may be used in combination. Of these, inorganic acid is preferable, hydrochloric acid and sulfuric acid are more preferable, and sulfuric acid is further preferable.

The production method of the present invention includes the third step of adding $N^\varepsilon$-lauroyl lysine to the aqueous solution obtained in the second step and filtering the mixture. With this step, the residue of $N^\varepsilon$-lauroyl lysine and/or a salt thereof in the finally-obtained aqueous solution can be reduced, and the generation of precipitate in the aqueous solution can be suppressed.

$N^\varepsilon$-lauroyl lysine to be added in the third step may be an L-form or D-form, preferably an L-form. The $N^\varepsilon$-lauroyl lysine may be a powder or crystal (seed crystal), preferably crystal. As the crystal of $N^\varepsilon$-lauroyl lysine, a commercially available product can be used, and can be obtained by a known crystallization method. The amount of the $N^\varepsilon$-lauroyl lysine to be added in the third step is preferably 0.02-0.04 mol, more preferably 0.025-0.03 mol, per 1 mol of the $N^\varepsilon$-lauroyl lysine and/or a salt thereof used in the first step (1 mol of the total of both when they are used).

After addition of $N^\varepsilon$-lauroyl lysine to the aqueous solution, the aqueous solution is preferably agitated for a given time. The stirring time is preferably 180-300 min, more preferably 210-240 min, and the temperature of the aqueous solution is preferably 15-30° C., more preferably 20-25° C.

In the third step, filtration is performed after addition of $N^\varepsilon$-lauroyl lysine. Examples of the filtration method include natural filtration, filtration under reduced pressure, pressure filtration and the like. Of these, filtration under reduced pressure or pressure filtration is preferable for improving the filtration rate.

Filtration under reduced pressure can be performed using a known vacuum apparatus such as aspirator, vacuum pump and the like and a known pressure resistant container in combination. The temperature of the aqueous solution during filtration under reduced pressure is preferably 20-60° C., more preferably 20-40° C.

Pressure filtration can be performed using a known apparatus such as stainless holder equipped with tank and the like. The pressure for pressure filtration is preferably 0.2-10 MPa, more preferably 0.3-5 MPa, and the temperature of the aqueous solution at that time is preferably 20-90° C., more preferably 40-80° C.

For filtration, a filter aid (e.g., Celite (registered trade mark) etc.) is preferably used. A method of using a filter aid is not particularly limited, and an aqueous solution may be filtered through a filter bedded with a filter aid, an aqueous solution added with a filter aid may be filtered, or an aqueous solution added with a filter aid may be filtered through a filter bedded with a filter aid.

When a filter aid is used by addition to an aqueous solution, an aqueous solution containing a filter aid is preferably agitated for a given time to ensure sufficient adsorption of impurities to the filter aid. The stirring time thereof is preferably 5-300 min, more preferably 10-200 min, and the temperature of the aqueous solution at that time is preferably 20-90° C., more preferably 40-80° C.

The production method of the present invention includes the fourth step of adjusting the aqueous solution obtained in the third step to pH 9-11. The pH is preferably 9.5-10.5, more preferably 9.8-10.2. The base to be used for pH adjustment is not particularly limited and, for example, sodium hydroxide, potassium hydroxide, calcium hydroxide, sodium carbonate, ammonia and the like can be mentioned. Only one kind of base may be used, or two or more kinds thereof may be used in combination. Of these, sodium hydroxide is preferable.

The production method of the present invention preferably further includes a step of putting the aqueous solution obtained in the fourth step in a container. The container is not particularly limited and, for example, any of bottle, can, bag and the like can be used. In addition, the material of the container is not particularly limited, and any of glass, plastic, metal, and a composite material thereof can be used.

The content of $N^\varepsilon$-lauroyl lysine and/or a salt thereof (total of both when they are present) in an aqueous solution obtained by the production method of the present invention (aqueous solution obtained in the fourth step) is preferably not more than 0.016 wt %, more preferably not more than 0.013 wt %, further preferably not more than 0.01 wt %. When the content is reduced, the generation of precipitate in the aqueous solution is suppressed.

The content of bis($N^\varepsilon$-lauroyl lysine)dicarboxylic acid diamide and/or a salt thereof (total of both when they are present) in an aqueous solution obtained by the production method of the present invention (aqueous solution obtained in the fourth step) is preferably 5-20 wt %, more preferably 7-15 wt %, further preferably 8-12 wt %.

An aqueous solution obtained by the production method of the present invention may contain ($N^\varepsilon$-lauroyl lysine)dicarboxylic acid monoamide and/or a salt thereof. The ($N^\varepsilon$-lauroyl lysine)dicarboxylic acid monoamide (hereinafter sometimes to be abbreviated as "monoamide") means a condensate formed in water by the reaction of 1 molecule of $N^\varepsilon$-lauroyl lysine with 1 molecule of dicarboxylic acid dichloride at the α position —$NH_2$ thereof, and the chemical structure thereof is represented by the following formula (2):

$$R^1-NH-CO-R^2-COOH \quad (2)$$

wherein $R^1$ is a monovalent organic group derived from $N^\varepsilon$-lauroyl lysine, and $R^2$ is a divalent organic group derived from dicarboxylic acid dichloride.

Examples of the monoamide include ($N^\varepsilon$-lauroyl lysine)oxalic acid monoamide, ($N^\varepsilon$-lauroyl lysine)malonic acid monoamide, ($N^\varepsilon$-lauroyl lysine)succinic acid monoamide, ($N^\varepsilon$-lauroyl lysine)glutaric acid monoamide, ($N^\varepsilon$-lauroyl lysine)adipic acid monoamide, ($N^\varepsilon$-lauroyl lysine)pimelic acid monoamide, ($N^\varepsilon$-lauroyl lysine)suberic acid monoamide, ($N^\varepsilon$-lauroyl lysine)azelaic acid monoamide, ($N^\varepsilon$-lauroyl lysine)sebacic acid monoamide, ($N^\varepsilon$-lauroyl lysine)undecanedioic acid monoamide, ($N^\varepsilon$-lauroyl lysine)dodecanedioic acid monoamide, ($N^\varepsilon$-lauroyl lysine)phthalic acid monoamide, ($N^\varepsilon$-lauroyl lysine)isophthalic acid monoamide, ($N^\varepsilon$-lauroyl lysine)terephthalic acid monoamide and the like. In one embodiment of the present invention, the monoamide is, for example, ($N^\varepsilon$-lauroyl lysine)suberic acid monoamide, ($N^\varepsilon$-lauroyl lysine)azelaic acid monoamide, or ($N^\varepsilon$-lauroyl lysine)sebacic acid monoamide. In another embodiment of the present invention, the monoamide is, for example, ($N^\varepsilon$-lauroyl lysine)sebacic acid monoamide.

The cation contained in the salt of the monoamide is derived from the base used for the $N^\varepsilon$-lauroyl lysine salt used in the first step and/or pH adjustment. In the salt of the monoamide, two carboxy groups may be in the form of a salt (—COOM, M is a counter cation), or only one carboxy group may be in the form of a salt. Examples of the salt of the monoamide include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt and the like. In one embodiment of the present invention, the salt of the monoamide is, for example, a sodium salt (monosodium salt and/or disodium salt). In another embodiment, the salt of the monoamide is, for example, a disodium salt. In another embodiment, the salt of the monoamide is, for example, a ($N^\varepsilon$-lauroyl lysine)sebacic acid monoamide disodium salt.

The content of ($N^\varepsilon$-lauroyl lysine)dicarboxylic acid monoamide and/or a salt thereof (total of both when they are present) in an aqueous solution is preferably not more than 1.0 wt %, more preferably 0.1-1.0 wt %, further preferably 0.2-0.6 wt %.

An aqueous solution obtained by the production method of the present invention may contain dicarboxylic acid and/or a salt thereof. The dicarboxylic acid is derived from the dicarboxylic acid dichloride used in the first step. Examples of the dicarboxylic acid include oxalic acid, malonic acid, succinic acid, glutaric acid, adipic acid, pimelic acid, suberic acid, azelaic acid, sebacic acid, undecanedioic acid, dodecanedioic acid, phthalic acid, isophthalic acid, terephthalic acid and the like. In one embodiment of the present invention, the dicarboxylic acid is, for example, suberic acid, azelaic acid, or sebacic acid. In another embodiment, the dicarboxylic acid is, for example, sebacic acid.

The cation contained in the salt of the dicarboxylic acid is derived from the base used for the $N^\varepsilon$-lauroyl lysine salt used in the first step and/or pH adjustment. In the salt of the dicarboxylic acid, two carboxy groups may be in the form of a salt (—COOM, M is a counter cation), or only one carboxy group may be in the form of a salt. Examples of the salt of the dicarboxylic acid include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt and the like. In one embodiment of the present invention, the salt of the dicarboxylic acid is, for example, sodium salt (monosodium salt and/or disodium salt). In another embodiment, the salt of the dicarboxylic acid is, for example, a disodium salt. In another embodiment, the salt of the dicarboxylic acid is, for example, sebacic acid disodium.

The content of dicarboxylic acid and/or a salt thereof (total of both when they are present) in an aqueous solution is preferably not more than 0.5 wt %, more preferably 0.01-0.5 wt %, further preferably 0.1-0.4 wt %.

The present invention also provides an aqueous solution comprising 5-20 wt % of bis($N^\varepsilon$-lauroyl lysine)dicarboxylic acid diamide and/or a salt thereof and having a pH of 9-11, wherein the content of the $N^\varepsilon$-lauroyl lysine and/or a salt thereof is not more than 0.016 wt %. The content of the ($N^\varepsilon$-lauroyl lysine)dicarboxylic acid monoamide and/or a salt thereof (total of both when they are present) in the aqueous solution of the present invention is preferably not more than 1.0 wt %. The content of dicarboxylic acid and/or a salt thereof (total of both when they are present) in the aqueous solution of the present invention is preferably not more than 0.5 wt %. The aqueous solution of the present invention is preferably put in a container. The aqueous solution of the present invention does not allow easy generation of precipitate, and is useful as a material for skin lotion and the like.

The aqueous solution of the present invention can be produced by the aforementioned method. The explanation of the components contained in the aqueous solution of the present invention (specific preferable examples, content etc.) and the explanation of the container in which the aqueous solution of the present invention is put are as mentioned above.

Other features of the invention will become apparent in the course of the following descriptions of exemplary embodiments which are given for illustration of the invention and are not intended to be limiting thereof.

EXAMPLES

The present invention is explained in more concretely in the following by referring to Examples, which are not to be construed as limitative. It is also possible to make appropriate modifications within the range in conformity with the above-mentioned and the below-mentioned gist, all of which are encompassed in the technical scope of the present invention.

Note that "%" and "parts" indicated in the following Examples mean "wt %" and "parts by weight", respectively, unless specifically described.

Example 1

$N^\varepsilon$-lauroyl-L-lysine (82.1 g), water (800 g), and 25% aqueous sodium hydroxide solution (100 g) were stirred at room temperature to dissolve $N^\varepsilon$-lauroyl-L-lysine (pH of water solvent=13.7), and sebacic acid dichloride (33.2 g) was added dropwise. The mixture was stirred at room temperature for 30 min, and the aqueous solution was adjusted to pH 8.0 with 75% sulfuric acid (5.5 g) while maintaining at 45° C. The temperature of the aqueous solution was decreased to 25° C., $N^\varepsilon$-lauroyl-L-lysine (seed crystal) (2.1 g) was added, and the mixture was stirred for 4 hr. The aqueous solution was filtered through Celite at room temperature (filtration under reduced pressure using diaphragm vacuum pump DIVAC 0.6 L, filter paper No. 5C for Kiriyama funnel), a 25% aqueous sodium hydroxide solution (0.2 g) was added to the filtrate (aqueous solution) to adjust the aqueous solution to pH 10, whereby an 10.3% aqueous solution (1021 g) of bis($N^\varepsilon$-lauroyl-L-lysine)sebacic acid diamide disodium salt was obtained (content of $N^\varepsilon$-lauroyl-L-lysine sodium salt in aqueous solution 0.010%, weight ratio of $N^\varepsilon$-lauroyl-L-lysine sodium salt/bis($N^\varepsilon$-lauroyl-L-lysine)sebacic acid diamide disodium salt=0.10/100). The obtained aqueous solution was colorless and transparent, and the appearance thereof did not change even after standing at room temperature for 2 weeks. The composition of the obtained aqueous solution was examined by HPLC and ion chromatography under the following conditions. While $N^\varepsilon$-lauroyl-L-lysine and the like are present as a sodium salt in the above-mentioned aqueous solution, since the HPLC measurement was performed under acidic conditions, the amount of a free form of $N^\varepsilon$-lauroyl-L-lysine and the like was measured. The content of the sodium salt in the aqueous solution was calculated from the amount of the free form measured by HPLC. The results are shown in Table 1.

HPLC
  instrument used: HPLC CLASS-LC10 series (manufactured by Shimadzu Corporation)
  separation column: YMC-Pack AM12S05-1506WT 6.0 mm×150 mm, particle size S-5, pore size 12 nm
  eluent: methanol:30 mM aqueous sodium dihydrogen phosphate solution (pH=3.0)=85:15 (volume ratio)
  flow rate: 1 ml/min
  column temperature: 40° C.
  injection volume: 10 μl
ion chromatography
  detection: 210 nm
  instrument used: Ion Chromato DX-100 (manufactured by Dionex)
analysis conditions
  separation column; AG11-HC 2.0 mm×50 mm+AS11-HS 2.0 mm×250 mm
  eluent: aqueous sodium hydroxide solution (sodium hydroxide concentration 0-20 min: 1.5 mM, 20-60 min: 30 mM)
  suppressor: AMMS-II 4 mm
  flow rate: 0.38 ml/min
  column temperature: 40° C.
  regenerant: dilute sulfuric acid ($H_2SO_4$ concentration 50 mM)
  regenerant flow rate: about 1 ml/min
  injection volume: 10 μl
  detection: electric conductivity
  standard solution: anion mixed standard solution IV for IC (manufactured by KANTO CHEMICAL CO., INC.)

TABLE 1

| component | content (%) |
| --- | --- |
| bis($N^\varepsilon$-lauroyl-L-lysine)sebacic acid diamide disodium salt | 10.3 |
| ($N^\varepsilon$-lauroyl-L-lysine)sebacic acid monoamide disodium salt | 0.36 |
| $N^\varepsilon$-lauroyl-L-lysine sodium salt | 0.010 |
| sebacic acid disodium | 0.30 |
| sodium chloride | 1.65 |
| sodium sulfate | 0.29 |

Comparative Example 1

In the same manner as in Example 1 except that the second and the third steps (i.e., adjusting pH of aqueous solution, addition of $N^\varepsilon$-lauroyl-L-lysine and filtration thereafter) were not performed, an aqueous solution of bis($N^\varepsilon$-lauroyl-L-lysine)sebacic acid diamide disodium salt was obtained.

To be specific, $N^\varepsilon$-lauroyl-L-lysine (82.1 g), water (800 g), and 25% aqueous sodium hydroxide solution (100 g) were stirred at room temperature to dissolve $N^\varepsilon$-lauroyl-L-lysine (pH of water solvent=13.7), and sebacic acid dichloride (33.2 g) was added dropwise. Thereafter, the aqueous solution was adjusted to pH 10 with 25% sodium hydroxide to give an 10.3% aqueous solution of bis($N^\varepsilon$-lauroyl-L-lysine)sebacic acid diamide disodium salt (content of $N^\varepsilon$-lauroyl-L-lysine sodium salt in aqueous solution 0.033%, weight ratio of $N^\varepsilon$-lauroyl-L-lysine sodium salt/bis($N^\varepsilon$-lauroyl-L-lysine)sebacic acid diamide disodium salt=0.32/100). While the obtained aqueous solution was colorless and transparent immediately after production, white precipitate was generated when stood at room temperature for 2 weeks. The precipitate was filtered, dried, and subjected to HPLC and measurement of $^1$H-NMR and IR under the following conditions to find that the precipitate was $N^\varepsilon$-lauroyl-L-lysine.

HPLC instrument used: HPLC CLASS-LC10 series (manufactured by Shimadzu Corporation)

separation column: YMC-Pack AM12S05-1506WT 6.0 mm×150 mm, particle size S-5, pore size 12 nm eluent: methanol:30 mM aqueous sodium dihydrogen phosphate solution (pH=3.0)=85:15 (volume ratio)

flow rate: 1 ml/min column temperature: 40° C.

injection volume: 10 µl detection: 210 nm $^1$H-NMR instrument used: AVANCE III HD NMR Spectrometer (manufactured by Bruker)

400 MHz solvent: acetic acid-d$_4$

IR (KBr method)

instrument used: IRPrestige-21 (manufactured by Shimadzu Corporation)

Comparative Example 2

In the same manner as in Example 1 except that $N^\varepsilon$-lauroyl-L-lysine was not added in the third step, an aqueous solution of bis($N^\varepsilon$-lauroyl-L-lysine)sebacic acid diamide disodium salt was obtained.

To be specific, $N^\varepsilon$-lauroyl-L-lysine (82.1 g), water (800 g), and 25% aqueous sodium hydroxide solution (100 g) were stirred at room temperature to dissolve $N^\varepsilon$-lauroyl-L-lysine (pH of water solvent=13.7), and sebacic acid dichloride (33.2 g) was added dropwise. The mixture was stirred at room temperature for 30 min, and the aqueous solution was adjusted to pH 8.0 with 75% sulfuric acid (5.5 g) while maintaining at 45° C. The temperature of the aqueous solution was decreased to 25° C., and the solution was stirred for 4 hr. The aqueous solution was filtered through Celite at room temperature (filtration under reduced pressure using diaphragm vacuum pump DIVAC 0.6 L, filter paper No. 5C for Kiriyama funnel), a 25% aqueous sodium hydroxide solution (0.2 g) was added to the filtrate (aqueous solution) to adjust the aqueous solution to pH 10, whereby an 10.3% aqueous solution of bis($N^\varepsilon$-lauroyl-L-lysine)sebacic acid diamide disodium salt was obtained (content of $N^\varepsilon$-lauroyl-L-lysine sodium salt in aqueous solution 0.026%, weight ratio of $N^\varepsilon$-lauroyl-L-lysine sodium salt/bis($N^\varepsilon$-lauroyl-L-lysine)sebacic acid diamide disodium salt=0.25/100). While the obtained aqueous solution was colorless and transparent immediately after production, white precipitate was generated when stood at room temperature for 2 weeks.

$N^\varepsilon$-lauroyl-L-lysine in the aqueous solutions obtained in Example 1 and Comparative Examples 1 and 2

The sodium salt content, and the appearance of the aqueous solutions immediately after production and after standing at room temperature for 2 weeks after production are shown in Table 2.

TABLE 2

| | content (%) of $N^\varepsilon$-lauroyl-L-lysine sodium salt in aqueous solution | appearance of aqueous solution | |
|---|---|---|---|
| | | immediately after production | 2 weeks later |
| Example 1 | 0.010 | ○ | ○ |
| Comparative Example 1 | 0.033 | ○ | X |
| Comparative Example 2 | 0.026 | ○ | X |

○: colorless transparent,
X: white precipitate

Examples 2 and 3, and Comparative Examples 3 and 4

The following experiment was performed, and the content of $N^\varepsilon$-lauroyl-L-lysine sodium salt in an aqueous solution free of white precipitate even after 2 weeks from production was examined.

To be specific, $N^\varepsilon$-lauroyl-L-lysine was added to the 10% aqueous solution of bis($N^\varepsilon$-lauroyl-L-lysine)sebacic acid diamide disodium salt produced in Example 1 to produce aqueous solutions of $N^\varepsilon$-lauroyl-L-lysine sodium salt having the contents shown in Table 3, and the appearance of the aqueous solution after standing at room temperature for 2 weeks after production were observed. The results are shown in Table 3.

TABLE 3

| | content (%) of $N^\varepsilon$-lauroyl-L-lysine sodium salt in aqueous solution | appearance of aqueous solution at 2 weeks after production |
|---|---|---|
| Example 2 | 0.013 | ○ |
| Example 3 | 0.016 | ○ |
| Comparative Example 3 | 0.017 | X |
| Comparative Example 4 | 0.019 | X |

○: colorless transparent,
X: white precipitate

Example 4 and Comparative Example 5

Using the aqueous solutions of Example 1 and Comparative Example 1 as a material, skin lotion was produced. The composition of the skin lotion, and the appearance of the skin lotion immediately after production and after standing at room temperature for 2 weeks after production are shown in Table 4.

TABLE 4

| | Example 4 | Comparative Example 5 |
|---|---|---|
| aqueous solution of Example 1 | 5 | — |
| aqueous solution of Comparative Example 1 | — | 5 |
| glycerol | 5 | 5 |
| 1,3-butylene glycol | 5 | 5 |
| ethanol | 5 | 5 |

TABLE 4-continued

|  |  | Example 4 | Comparative Example 5 |
|---|---|---|---|
| methylparaben |  | 0.1 | 0.1 |
| phenoxyethanol |  | 0.3 | 0.3 |
| citric acid |  | amount to adjust skin lotion to pH 7 | amount to adjust skin lotion to pH 7 |
| water |  | amount to make total of skin lotion 100 parts | amount to make total of skin lotion 100 parts |
| appearance of skin lotion | immediately after production | ○ | ○ |
|  | 2 weeks later | ○ | X | unit of component amount: parts
○: colorless transparent,
X: white precipitate

INDUSTRIAL APPLICABILITY

The aqueous solution of the present invention containing bis($N^\varepsilon$-lauroyl lysine)dicarboxylic acid diamide and/or a salt thereof is useful as a material for skin lotion and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of producing an aqueous solution, comprising at least one bis($N^\varepsilon$-lauroyl lysine)dicarboxylic acid diamide and/or a salt thereof, and having a pH of 9 to 11, said method comprising:
   (1) reacting $N^\varepsilon$-lauroyl lysine and/or a salt thereof with at least one dicarboxylic acid dichloride in a water solvent having a pH of 12 to 14, to obtain a first aqueous solution comprising at least one bis($N^\varepsilon$-lauroyl lysine) dicarboxylic acid diamide and/or a salt thereof;
   (2) adjusting the pH of said first aqueous solution to obtain a second aqueous solution having a pH of 7.5 to 8.5;
   (3) adding $N^\varepsilon$-lauroyl lysine to said second aqueous solution and filtering the resulting mixture, to obtain a third aqueous solution; and
   (4) adjusting the pH of said third aqueous solution to a value of pH 9 to 11.

2. The method according to claim 1, wherein said water solvent is substantially free of a hydrophilic organic solvent.

3. The method according to claim 1, wherein said aqueous solution obtained in said (4) adjusting contains $N^\varepsilon$-lauroyl lysine and/or a salt thereof in an amount of not more than 0.016 wt %, based on the total weight of said aqueous solution, and contains said at least one bis($N^\varepsilon$-lauroyl lysine) dicarboxylic acid diamide and/or a salt thereof in an amount of 5 to 20 wt %, based-on the total weight of said aqueous solution.

4. The method according to claim 2, wherein said aqueous solution obtained in said (4) adjusting contains $N^\varepsilon$-lauroyl lysine and/or a salt thereof in an amount of not more than 0.016 wt %, based on the total weight of said aqueous solution, and contains said at least one bis($N^\varepsilon$-lauroyl lysine) dicarboxylic acid diamide and/or a salt thereof in an amount of 5 to 20 wt %, based on the total weight of said aqueous solution.

5. The method according to claim 1, wherein said $N^\varepsilon$-lauroyl lysine and/or a salt thereof is a sodium salt of $N^\varepsilon$-lauroyl lysine.

6. The method according to claim 1, wherein said at least one dicarboxylic acid dichloride is at least one member selected from the group consisting of suberic acid dichloride, azelaic acid dichloride, and sebacic acid dichloride.

7. The method according to claim 1, wherein said at least one bis($N^\varepsilon$-lauroyl lysine)dicarboxylic acid diamide is bis ($N^\varepsilon$-lauroyl lysine)suberic acid diamide, bis($N^\varepsilon$-lauroyl lysine)azelaic acid diamide, or bis($N^\varepsilon$-lauroyl lysine)sebacic acid diamide.

8. The method according to claim 1, wherein said at least one bis($N^\varepsilon$-lauroyl lysine)dicarboxylic acid diamide is bis ($N^\varepsilon$-lauroyl lysine)sebacic acid diamide.

9. An aqueous solution, comprising 5 to 20 wt % of at least one bis($N^\varepsilon$-lauroyl lysine)dicarboxylic acid diamide and/or a salt thereof and having a pH of 9 to 11, which comprises $N^\varepsilon$-lauroyl lysine and/or a salt thereof in an amount of not more than 0.016 wt %, based on the total weight of said aqueous solution.

10. The aqueous solution according to claim 9, which comprises ($N^\varepsilon$-lauroyl lysine)dicarboxylic acid monoamide and/or a salt thereof in an amount of not more than 1.0 wt %, based on the total weight of said aqueous solution.

11. The aqueous solution according to claim 9, which comprises a dicarboxylic acid and/or a salt thereof in an amount of not more than 0.5 wt %, based on the total weight of said aqueous solution.

12. The aqueous solution according to claim 10, which comprises a dicarboxylic acid and/or a salt thereof in an amount of not more than 0.5 wt %, based on the total weight of said aqueous solution.

13. The aqueous solution according to claim 9, which is contained in a container.

14. The aqueous solution according to claim 9, wherein said $N^\varepsilon$-lauroyl lysine and/or a salt thereof is a sodium salt of $N^\varepsilon$-lauroyl lysine.

15. The aqueous solution according to claim 9, wherein said dicarboxylic acid is at least one member selected from the group consisting of suberic acid, azelaic acid, and sebacic acid.

16. The aqueous solution according to claim 9, wherein said at least one bis($N^\varepsilon$-lauroyl lysine)dicarboxylic acid diamide is bis($N^\varepsilon$-lauroyl lysine)suberic acid diamide, bis ($N^\varepsilon$-lauroyl lysine)azelaic acid diamide, or bis($N^\varepsilon$-lauroyl lysine)sebacic acid diamide.

17. The aqueous solution according to claim 9, wherein said at least one bis($N^\varepsilon$-lauroyl lysine)dicarboxylic acid diamide is bis($N^\varepsilon$-lauroyl lysine)sebacic acid diamide.

* * * * *

UNITED STATES PATENT AND TRADEMARK OFFICE
CERTIFICATE OF CORRECTION

PATENT NO. : 10,202,333 B2
APPLICATION NO. : 15/481022
DATED : February 12, 2019
INVENTOR(S) : Kobayashi Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 117 days.

Signed and Sealed this
Twenty-fourth Day of September, 2019

Andrei Iancu
*Director of the United States Patent and Trademark Office*